United States Patent [19]

Bauer et al.

[11] Patent Number: 5,306,302
[45] Date of Patent: Apr. 26, 1994

[54] IMPLANT MATERIAL

[75] Inventors: Hans J. Bauer, Reinheim; Bianca Katzenmeier, Weiterstadt; Matthias Kuntz, Mühltal-Traisa, all of Fed. Rep. of Germany

[73] Assignee: Merck Patent Gesellschaft mit beschränkter Haftung, Darmstadt, Fed. Rep. of Germany

[21] Appl. No.: 756,744

[22] Filed: Sep. 9, 1991

[30] Foreign Application Priority Data

Sep. 10, 1990 [DE] Fed. Rep. of Germany ....... 4028683

[51] Int. Cl.$^5$ .......................... A61F 2/28; A61F 2/02; A61F 2/30
[52] U.S. Cl. ........................................ 623/16; 623/11; 623/18
[58] Field of Search ................ 623/18, 16, 11; 427/2; 424/422, 423, 424

[56] References Cited

U.S. PATENT DOCUMENTS

| 4,314,380 | 2/1982 | Miyata et al. | 623/16 |
| 4,330,514 | 5/1982 | Nagai et al. | 623/16 X |
| 4,861,733 | 8/1989 | White | 501/1 |
| 5,133,756 | 7/1992 | Bauer et al. | 623/16 |
| 5,137,534 | 8/1992 | Sumita | 623/16 |

Primary Examiner—Randall L. Green
Assistant Examiner—Dinh X. Nguyen
Attorney, Agent, or Firm—Millen, White, Zelano, & Branigan

[57] ABSTRACT

The invention relates to an implant material based on natural bone, which material is a sintered ceramic material in which the porous fine structure of the bone is present in essentially unchanged form and which comprises more than 99% of hydroxyapatite.

18 Claims, No Drawings

IMPLANT MATERIAL

SUMMARY OF THE INVENTION

The invention relates to an implant material based on bone ceramic.

The requirement of efficient medical implant material for bone replacement is that it has a high mechanical stability. Implant materials based on minerals usually only ensure a high mechanical stability if they are employed as ceramics, i.e., in the form of materials or workpieces sintered at sufficiently high temperatures.

For the healing process, implant materials which have a high bioactivity, that is to say that they are accepted by the body and integrated into it, are regarded as particularly favorable. In the case of bone replacement material, this means that it should soon coalesce firmly and permanently with endogenous tissue, in particular with the bone.

Bone replacement materials based on calcium phosphate ceramics are considered to be bioactive owing to their chemical relationship with the mineral phase of natural bone. In its mineral phase, natural bone consists mainly of hydroxyapatite, a calcium phosphate of the molecular formula $Ca_5(PO_4)_3OH$.

Hydroxyapatite of synthetic or organic origin, for example, from natural bone material, is therefore a frequently used raw material for the production of implants for bone replacement. Hydroxyapatite ceramic cannot be substantially absorbed in the body. This means that exogenous material remains virtually unchanged over a long period and integration into the body essentially takes place by coalescence with existing bone and fusion into surrounding tissue.

The currently available ceramic implant materials based on calcium phosphate are divided into two basic groups.

The first group uses synthetically prepared calcium phosphates, which are shaped to give compact or porous bodies and then sintered to give the ceramic. The advantage of these materials naturally lies in the fact that the synthetic structure makes specific chemical compositions possible without problems and with great exactness and reproducibility. The standardizability of the composition is indispensable for medical applications.

The strength of the coalescence of compact calcium phosphate ceramic with existing bone is mainly unsatisfactory according to experience. Porous calcium phosphate ceramics exhibit more favorable fusion behavior.

A crucial disadvantage of synthetic materials is that porous articles can only be produced with great difficulty and high expenditure. It is not possible to this day using synthetic materials to provide molded articles with the porosity characteristic of natural bone, in particular, for example, the open porosity of cancellous bone. Cancellous bones have reticular, spongy or lattice-like structure. However, it has also emerged that just this porosity, typical of bone, is essential for rapid, solid and permanent combination of implant with the endogenous bone.

The second group is based on natural bone which is mineralized by various treatments and converted into a ceramic system in which the structure of the bone should be retained if possible. The removal of the organic bone constituents and the subsequent solidification to give the ceramic by sintering at appropriate temperatures are common to the processes. The removal of the organic constituents is carried out by chemical dissolving processes or by pyrolytic processes. Owing to their excellent correspondence to the pore system of natural bone, bone ceramic implants exhibit considerable biological advantages in fusion behavior and healing in the body.

A disadvantage of bone ceramic is that the natural product bone employed as a starting material is subject to considerably naturally-caused and uncontrollable variations in the chemical composition of its mineral phase. The mineral phase of bones thus consists mainly of hydroxyapatite, but also contains varying amounts of other calcium phosphate phases, trace elements and, in particular, of calcium carbonate varying from animal species to animal species, even from individual to individual. Thus, for example, horse bones in general have a distinctly higher content of calcium carbonate than bones from cattle. The calcium carbonate content of bones can vary throughout the range between 1 and 25% by weight.

It is therefore virtually impossible to assume a constant uniform chemical composition in the starting material, which would be necessary to obtain a standardized bone ceramic product. Such variations in the composition have quite clearly detectable influences on the biological activity of the bone ceramic implant. Thus, in the body, the pH of the medium surrounding the implant is influenced by the content of calcium oxide formed by the burning of calcium carbonate, which is manifested clinically in different fusion and bone formation rates.

As a particular problem, it has additionally emerged that bone ceramic has a tendency for uncontrolled instability. Both in storage and in the body, strength losses which lead up to disintegration can occur in bone ceramic implants after a varying and unforeseeable period.

An objective of the present invention was therefore based on developing an implant material based on bone ceramic which did not have the disadvantages of changing chemical composition, subject to natural variations, and unforeseeable instability.

Upon further study of the specification and appended claims, further objects and advantages of this invention will become apparent to those skilled in the art.

It has now been found that a bone ceramic can be obtained in which the porous fine structure of the bone is present in essentially unchanged form and which comprises, independently of the chemical composition of the mineral phase of the original bone, more than 99% of hydroxyapatite if bone material freed from all organic constituents is subjected to treatment with an aqueous solution of an organic acid from the group comprising the aliphatic $C_{1-5}$-monocarboxylic acids and malonic acid, tartronic acid, succinic acid, malic acid, tartaric acid and citric acid and then sintered to give the ceramic. A bone ceramic of constant, defined composition is thus obtainable in this manner.

Surprisingly, a material of this type does not exhibit the instability of conventional bone ceramic.

The invention thus relates to an implant material based on natural bone, which material is a sintered ceramic material in which the porous fine structure of the bone is present in essentially unchanged form and which comprises more than 99% of hydroxyapatite.

The invention also relates to a process for the production of such a bone ceramic implant material, in which bone material freed from all organic constituents is subjected to treatment with an aqueous solution of an organic acid from the group comprising the aliphatic $C_{1-5}$-monocarboxylic acids and malonic acid, tartronic acid, succinic acid, malic acid, tartaric acid and citric acid and is then sintered at temperatures between 900° and 1400° C.

Investigations of the instability of customary bone ceramics have shown that the access of moisture appears to be a trigger for the instability. For the period of storage, this problem could admittedly be solved by moisture-tight packaging of the ceramic, but not after surgical application, after which the bone ceramic implant is naturally exposed to the aqueous medium of the body. The changing contents of calcium carbonate in the original bone material were identified as responsible for the instability, it being possible to regard the following mechanism as probable: during the thermal treatment steps in the conversion of the bone to the ceramic, calcium carbonate present in the mineral phase is converted into calcium oxide. Calcium oxide phases are thus then present in the sintered ceramic in a stoichiometrically equivalent ratio. On access of water, for example, in the form of atmospheric humidity during unprotected storage or in the body after implantation, a successive conversion of calcium oxide to calcium hydroxide occurs according to the equation $$CaO + H_2O \rightarrow Ca(OH)_2$$

An increase in volume in the calcium oxide phases accompanies this conversion, which increase is about 97% on the basis of calculation. As a result, gradual tensions and hair cracks are produced in the ceramic material which can lead to swelling and breaking and even to the disintegration of the ceramic into individual particles.

In the process according to the invention, all amounts of calcium carbonate and possibly calcium oxide present and also, if present, minor amounts of other soluble contents are dissolved from the mineralized bone before sintering to give the ceramic. The acid treatment is expediently carried out using aqueous solutions of weak organic acids. Suitable acids for this purpose are primarily aliphatic $C_{1-5}$-monocarboxylic acids, aliphatic di- and tri-carboxylic acids and their hydroxy derivatives, each having altogether up to 6 C atoms. Examples of such acids are formic acid, acetic acid, propionic acid, butyric acid, valeric acid, malonic acid, tartronic acid, succinic acid, malic acid, tartaric acid and citric acid.

Citric acid has proved particularly suitable, as it is easily available, inexpensive and extremely problem-free to process.

The use concentration of the acid solutions to be selected depends on the nature and acid strength of the acid, the intended treatment period, the temperature and the manner in which the bone material was pretreated. In general, the use concentration is between 1 and 30% by weight, preferably between 5 and 10% by weight. The temperature of the acid solution can be freely adjusted between 20° C. and boiling temperature. A treatment period of between 2 minutes and 24 hours is adequate, depending on the amount of bone material to be treated, the size of the pieces and the above-mentioned parameters. From the preceding outline conditions, the person skilled in the art can determine the most suitable process parameters in each case without difficulty by means of a few routine tests.

All in all, the parameters given for the acid treatment are only to be considered as rough guidelines, which, if exceeded or fallen short of, in general have no other disadvantageous effect if it is ensured that any calcium oxide is removed.

Firstly, the bone serving as a starting material has to be completely demineralized, i.e., freed of all organic constituents. This can begin with the mechanical elimination of, for example, still adherent soft parts, but always comprises the removal of the organic phase of the bone, which essentially consists of collagen. Various procedures are known for this removal. The latter can be carried out, for example, by chemical solution and extraction processes, for example, by boiling and/or treatment with fat- or protein-dissolving solvents and/or treatment with hydrogen peroxide. Pyrolytic processes, however, have proved particularly simple and effective. In these processes, the organic constituent of the bone is decomposed by the action of heat and the resulting carbon is burned in an excess of oxygen. Temperatures between 500° and 1000° C., principally between 600° and 800° C., are customary for the pyrolysis of bone. Chemical solution processes and pyrolysis processes can also be combined to mineralize the bone material. In all of these processes, care has to be taken that the porous fine structure of the natural bone is retained as far as possible. For the bone ceramic implant material according to the invention, it is essential that this structure remains essentially unchanged, so the measures mentioned should be carried out as gently as possible. For the pyrolysis, therefore, a process according to DE-PS 3,727,606 can be employed in which special control of temperature and reductive or oxidative character of the atmosphere makes possible an extremely gentle pyrolysis.

It has proved advantageous to subject the bone material to presintering before the acid treatment. The structure in the mineral phase of the bone is strengthened by means of this, so that the stresses of the $CO_2$ evolution occurring during the acid treatment are survived without damage. This is particularly important in cancellous bone, whose highly porous delicate structure is naturally particularly sensitive.

Presintering is expediently carried out at temperatures between 600° and 1000° C., preferably around 900° C.

If presintering is necessary, it is expedient to execute this step immediately after the pyrolysis step and thus to carry out both steps in a combined operation.

For the acid treatment, it is sufficient to pass the bone material pretreated in this way into a bath of the acid solution and to store it there for a period and at a temperature appearing to be adequate and expedient. Recirculation of the acid solution can promote the dissolving out of the soluble constituents.

After acid treatment has been completed, the bone material is washed free of acid, expediently with demineralized water.

Final sintering to give the ceramic is then carried out according to customary processes and in devices which are conventional for this purpose. Sinter temperatures between 900 and 1400 C are adequate for this. Typically, the material is heated at about 100.C/h to the final temperature, for example, 1250.C, kept at this temperature for about 3 to 5 h and then cooled freely.

The bone ceramic thus obtained comprises chemically more than 99% of hydroxyapatite, which can be clearly detected by X-ray, owing to the accuracy of this method of investigation. In particular, it no longer contains any more amounts of calcium oxide, which is the cause of the instability of conventional bone ceramic.

The bone ceramic implant material according to the invention combined in a hitherto unprecedented manner the advantageous fusion behavior owing to the essentially unchanged existing porous structure of the underlying bone with the constantly defined chemical composition hitherto not achieved for such materials, that is to say of hydroxyapatite of more than 99% purity. In particular, the problem of incalculable instability no longer occurs in the material according to the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 28 683.5, are hereby incorporated by reference.

EXAMPLES

EXAMPLE 1

Raw cattle bones freed from soft parts were cut up by means of a saw and boiled 3 times with water for about 1 h. The pieces of bone were then heated to 450° C. under a nitrogen atmosphere at 50° C./h. During a subsequent heating period at 25° C./h to 750° C., the atmosphere was changed over in a linear manner to atmospheric oxygen and kept at this temperature for a further 8 h. Subsequently, heating was carried out at 50° C./h to a presinter temperature of 900° C. After cooling, the pieces were transferred to a recirculated 5% by weight citric acid solution for 3 h.

After removal from the acid bath, they were washed until neutral with demineralized water. For final sintering, the pieces were heated to 1250° C. at 100° C./h, kept at this temperature for 3 h and then cooled freely.

The pieces of bone ceramic obtained exhibit the unchanged porous structure of the original bone. The ceramic contains more than 99% of hydroxyapatite by X-ray.

EXAMPLE 2

In the case of identical treatment of horse bones, a bone ceramic was obtained which likewise contains more than 99% of hydroxyapatite.

EXAMPLE 3 (COMPARISON)

Horse bones were subjected to the same treatment as in Example 1, but the acid treatment was omitted. The bone ceramic obtained contains about 10% of calcium oxide by X-ray.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for production of an implant material based on natural bone, said implant material comprising a sintered ceramic material having a porous fine structure characteristic of natural bone in essentially unchanged form, and wherein more than 99% of said ceramic material is hydroxyapatite detectable by X-ray, said process comprising
    (a) subjecting bone material freed from all organic constituents to treatment with an aqueous solution of an organic acid selected from aliphatic $C_{1-5}$-monocarboxylic acid and malonic acid, tartronic acid, succinic acid, malic acid, tartaric acid and citric acid, and
    (b) sintering the bone material at temperatures between 900° and 1400° C. thereafter.

2. A process according to claim 1, wherein the acid treatment is carried out using an aqueous solution which contains 1 to 30% by weight of the organic acid.

3. A process according to claim 1, wherein the acid treatment is carried out using an aqueous solution which contains 5 to 10% by weight of the organic acid.

4. A process according to claim 1, wherein the acid treatment is carried out for a period of 2 minutes to 24 hours at a temperature between 20° C. and boiling temperature.

5. A process according to claim 1, wherein the acid treatment is carried out using an aqueous solution of citric acid.

6. A process according to claim 1, wherein the acid treatment is carried out using a recirculated aqueous solution of citric acid.

7. A process according to claim 1, further comprising subjecting the bone material to presintering at temperatures between 600° and 1000° C. before the acid treatment.

8. A process according to claim 1, wherein bone is freed of all organic constituents by chemical solution and extraction treatment.

9. A process according to claim 8, wherein bone is freed of all organic constituents selected from boiling and/or treatment with fat or protein dissolving solvents and/or treatment with $H_2O_2$.

10. A process according to claim 12, wherein said pyrolytic treatment is conducted at a temperature of 500°-1000° C.

11. A process according to claim 12, wherein said pyrolytic treatment is conducted at a temperature of 600°-800° C.

12. A process according to claim 1, wherein bone is freed of all organic constituents by pyrolytic treatment.

13. A process according to claim 1, wherein the bone is cancellous.

14. A process for production of an implant material based on natural bone, said implant material comprising a sintered ceramic material having a porous fine structure characteristic of natural bone in essentially unchanged form, and wherein more than 99% of said ceramic material is hydroxyapatite by X-ray, said process comprising
    (a) pyrolyzing bone material between 500° and 1000° C.,
    (b) subjecting the bone material freed from all organic constituents to treatment with an aqueous solution of an organic acid selected from aliphatic $C_{1-5}$-monocarboxylic acid and malonic acid, tartronic acid, succinic acid, malic acid, tartaric acid and citric acid, and (c) sintering the bone material at temperatures between 900° and 1400° C. thereafter.

15. A process according to claim 14, wherein the bone is cancellous.

16. A sintered ceramic implant material based on natural bone having a porous fine structure characteristic of natural bone comprising: more than 99% of hydroxyapatite, said hydroxyapatite detectable by X-ray, wherein said porous fine structure is present in the ceramic implant material in essentially unchanged form.

17. An implant material according to claim 16, wherein said bone is cancellous.

18. An implant material according to claim 16, wherein said ceramic material contains no amounts of calcium oxide.

* * * * *